(12) United States Patent
Burd et al.

(10) Patent No.: US 7,659,105 B2
(45) Date of Patent: Feb. 9, 2010

(54) METHODS AND COMPOSITIONS FOR BUTANOL PRODUCTION

(75) Inventors: Genrich Burd, Oak Park, IL (US); Anamitra Bhattacharyya, Evanston, IL (US)

(73) Assignee: Integrated Genomics, Inc., Arlington Heights, IL (US)

( * ) Notice: Subject to any disclaimer, the term of this patent is extended or adjusted under 35 U.S.C. 154(b) by 0 days.

(21) Appl. No.: 12/346,555

(22) Filed: Dec. 30, 2008

(65) Prior Publication Data

US 2009/0176288 A1 Jul. 9, 2009

Related U.S. Application Data

(63) Continuation-in-part of application No. PCT/US2007/072883, filed on Jul. 5, 2007.

(60) Provisional application No. 60/818,667, filed on Jul. 6, 2006.

(51) Int. Cl.
  *C12N 1/20* (2006.01)
(52) U.S. Cl. ................. 435/252.3; 435/252.33
(58) Field of Classification Search ............... None
  See application file for complete search history.

(56) References Cited

U.S. PATENT DOCUMENTS

2008/0182308 A1   7/2008   Donaldson et al.

FOREIGN PATENT DOCUMENTS

WO   WO 2007/041269 A1   4/2007

*Primary Examiner*—Nashaat T Nashed
(74) *Attorney, Agent, or Firm*—Teddy Scott, Jr.; Toff S. Hofmeister; Polsinelli Shughart PC

(57) ABSTRACT

A butanol producing cell and a method for the production of butanol are provided. Butanol producing cells comprising a butanol synthesis system or butanol export proteins may be used to enhance the production of butanol from a carbon substrate composition.

13 Claims, 3 Drawing Sheets

METHODS AND COMPOSITIONS FOR BUTANOL PRODUCTION

CROSS-RELATED APPLICATIONS

This is a continuation-in-part of PCT/US2007/072883 filed on Jul. 5, 2007, which claims the benefit of U.S. provisional application 60/818,667, filed on Jul. 6, 2006, the contents each of which are incorporated by reference.

FIELD OF THE INVENTION

The present invention relates to methods and compositions for the production of butanol.

BACKGROUND

The production of butanol by solvent-producing strains of *Clostridium* spp. was one of the most important biotechnological developments in the first half of the 20th Century. Butanol is currently used as a chemical in the production of lacquers, plasticizers, coatings, detergents, and brake fluids. Furthermore, it is useful as a chemical substrate in the plastics industry and as a fuel additive. There is a growing interest in enhancing butanol production via butanol fermentation in bacteria. However, end-product inhibition is often a barrier to efficient productivity in many industrial fermentation processes. This toxicity results in lower than ideal final titers of butanol.

Attempts have been made to adapt fermenting bacteria to growth-limiting conditions. Toxic solvents induce the synthesis of heat shock proteins. The overexpression of heat shock proteins GroESL in *Clostridium acetobutylicum* results in less inhibition of clostridial growth by butanol challenge and increased final solvent titers. However, the cells are sensitive to low concentrations of butanol.

Efforts to obtain mutants that can tolerate and produce higher concentrations of butanol have been met with limited success. Butanol toxicity may have multiple effects on the cell. While there have been a few butanol-tolerant mutants to produce higher concentrations of solvent than their respective parent strains, none have been able to produce desired solvent levels.

There remains a need for the development of strains that have enhanced butanol end product tolerance and therefore can produce industrially viable concentrations of butanol.

SUMMARY

Provided herein is a microbial cell capable of being used for producing butanol. The butanol-producing microbial cell may export butanol via export proteins. The cell may comprise a butanol synthesis system and/or a butanol export protein. The cell may express components of the butanol synthesis system and the butanol export protein from heterologous nucleic acid or from endogenous nucleic acid. Components of the butanol synthesis system may comprise enzymes that catalyze reactions, including the conversion of acetyl-CoA to acetoacetyl-CoA; the coversion of acetoacetyl-CoA to 3-hydroxybutyryl-CoA; the conversion of 3-hydroxybutyryl-CoA to crotonyl-CoA; the conversion of crotonyl-CoA to butyryl-CoA; the conversion of butyryl-CoA to butyraldehyde; and the conversion of butyraldehyde to 1-butanol. The enzymes may include acetyl-CoA acetyl transferase, 3-hydroxybutyryl-CoA dehydrogenase, crotonase, butyryl-CoA dehydrogenase, butyraldehyde dehydrogenase, and butanol dehydrogenase.

The butanol export protein may be a multi-drug resistance protein. The butanol export protein may be an OmrA protein and/or a LmrA protein. The butanol-producing cell may be resistant to toxicity associated with intracellular or extracellular butanol. The resistance may be associated with the export protein. An increased resistance to butanol may be associated with the export protein. The resistance may be associated with butanol feedback inhibition of the strain. A butanol-producing cell that is resistant to butanol-associated toxicity may be the microbial cell deposited in ATCC (*C. acetobutylicum* BUT R/1; ATCC No. PTA-8515). The ATCC No. PTA-8515 cell may express a heterologous nucleic acid encoding an export protein. The export protein may be OmrA or LmrA. The export protein may increase ATCC No. PTA-8515 butanol resistance.

A method of using the butanol-producing cells to produce a butanol is also provided herein. The butanol-producing cell may be contacted with a carbon substrate under suitable conditions for the cell to produce butanol.

DETAILED DESCRIPTION

Figure 1:
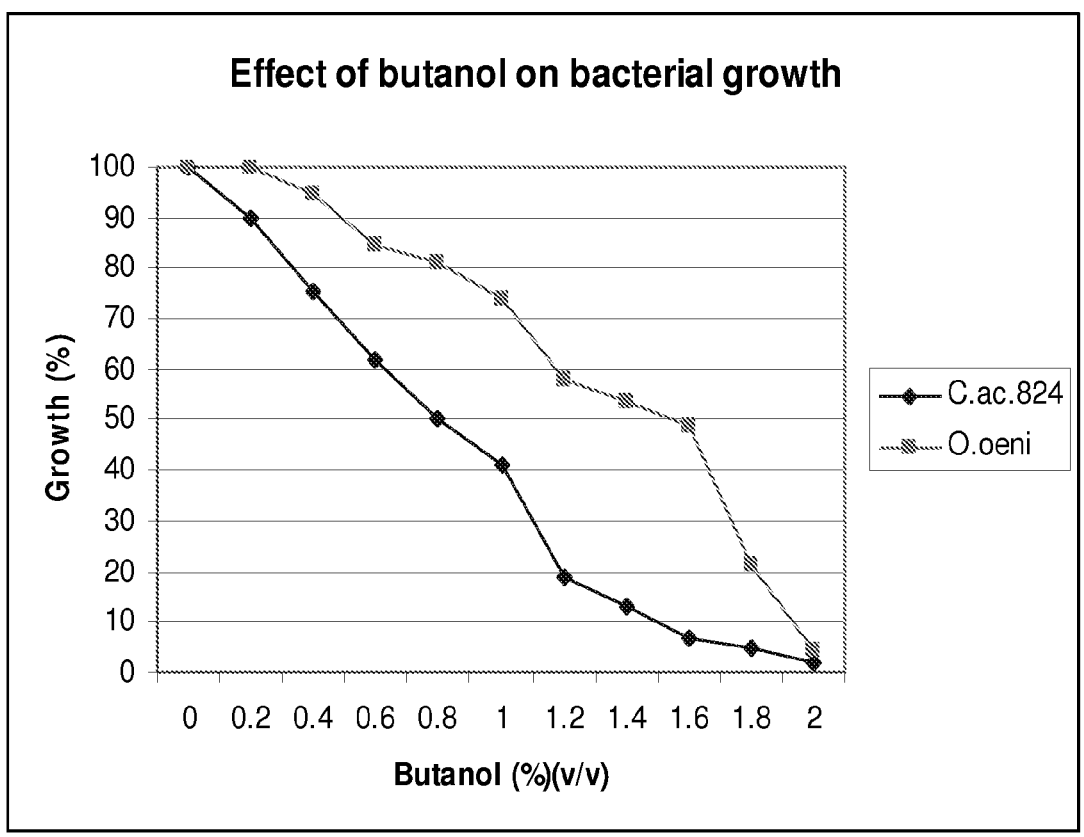
FIG. 1 shows the varying sensitivity of *Clostridium acetobutylicum* and *Oenococcus oeni* toward butanol. *O. oeni* is significantly more resistant to butanol than *C. acetobutylicum*.

Current methods for producing high levels of butanol via fermentation in microbial cell are inefficient, in part, due to end product inhibition. Provided herein is a butanol producing microbial cell with increased resistance to inhibition and/or toxicity of increased levels of butanol end product. A butanol concentration of 13 g/liter in a fermentation broth can be toxic to fermenting cells. This cell may allow for a more efficient production of butanol at an industrial scale.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6,9, and 7.0 are explicitly contemplated.

a. Carbon Substrate

"Carbon substrate" or "fermentable carbon substrate" as used herein may mean a carbon source capable of being metabolized by host organisms of the present invention. Representative carbon sources include monosaccharides, oligosaccharides, polysaccharides, and one-carbon substrates or mixtures thereof.

b. Cloning Site

"Cloning site" as used herein may mean a region that allows for the insertion of desired nucleic acid sequences.

Typically, the cloning site comprises one or more restriction endonuclease recognition sites. Cloning sites may include multiple cloning sites or polylinkers.

c. Gene

"Gene" as used herein may mean a nucleic acid that expresses an encoded polypeptide, including regulatory sequences preceding (5' non-coding) and following (3' non-coding) the coding region. The terms "native" and "wild-type" may refer to a gene as found in nature with its own regulatory sequences.

d. Heterologous DNA

"Heterologous DNA," "foreign gene", "foreign DNA", and "heterologous gene" as used herein may mean genetic material native to one organism that has been placed within a host organism by various means. The gene of interest may be a naturally occurring gene, a mutated gene or a synthetic gene.

e. Isolated

"Isolated" as used herein may mean a protein or nucleic acid sequence that is removed from at least one component with which it is naturally associated.

f. Nucleic Acid

"Nucleic acid" as used herein may mean a nucleic acid that may be employed at any length, with the total length being limited by the ease of preparation and use in the intended protocol. Illustrative nucleic acid segments may be useful with total lengths of about 10,000, about 5000, about 3000, about 2,000, about 1,000, about 500, about 200, about 100, about 50 base pairs in length, and the like.

g. Origin of Replication

"Origin of replication" as used herein may mean a nucleic acid sequence that is necessary to allow replication of a vector within an organism.

h. Promoter

"Promoter" as used herein may mean a nucleic acid to which ribonucleic acid polymerase binds to initiate the transcription of a nucleic acid sequences linked to the promoter.

i. Recombinant Organism

"Recombinant organism" and "transformed host" as used herein may mean any organism having been transformed with heterologous or foreign genes or extra copies of homologous genes.

j. Substantially Complementary

"Substantially complementary" as used herein may mean that a first sequence is at least 50%-90%, or 90%-99% identical to the complement of a second sequence over a a region of 8-10, 10-100, or 100-350 or more nucleotides or amino acids nucleotides, or amino acids. Intermediate lengths may mean any length between the quoted values, such as 16-153, 200-1,000 etc.; including 200-500; 500-1,000, and the like. Substantial complementary may also mean that two nucleotide sequences hybridize under stringent hybridization conditions using the methods described herein.

k. Substantially Identical

"Substantially identical" as used herein may mean that a first and second nucleotide or amino acid sequence are at least about 60%-90%, or 90%-99% identical over a region of 8-10, 10-100, or 100-350 or more nucleotides or amino acids. Intermediate lengths may mean any length between the quoted values, such as 16-153; including 200-500; 500-1,000, and the like. Substantially identical may also mean the first sequence nucleotide or amino acid sequence is substantially complementary to the complement of the second sequence.

l. Transformation

"Transformation" as used herein may mean the process of introducing nucleic acid into an organism that changes the genotype of the recipient organism (i.e. the acquisition of a new gene in a cell after the incorporation of nucleic acid. The acquired gene may be integrated into chromosomal DNA or introduced as an extrachromosomal replicating sequence.) The term "transformant" refers to the product of a transformation.

m. Variant

"Variant" as used herein in the context of a nucleic acid may mean a substantially identical or substantially complementary sequence. A variant in reference to a nucleic acid may further mean a nucleic acid that may contain one or more substitutions, additions, deletions, insertions, or may be fragments thereof. A variant may also be a nucleic acid capable of hybridizing under moderately stringent conditions. Hybridization techniques are well known and may be conducted under moderately stringent conditions.

A variant in reference to a peptide may further mean differing from a native peptide in one or more substitutions, deletions, additions and/or insertions, or a sequence substantially identical to the native peptide sequence. The ability of a variant to react with antigen-specific antisera may be enhanced or unchanged, relative to the native protein, or may be diminished by less than 50%, or less than 20%, relative to the native peptide. Such variants may generally be identified by modifying one of the peptide sequences encoding an agent and evaluating the reactivity of the modified peptide with antigen-specific antibodies or antisera as described herein. Variants may include those in which one or more portions have been removed such as an N-terminal leader sequence or transmembrane domain. Other variants may include variants in which a small portion (e.g., 1-30 amino acids, or 5-15 amino acids) has been removed from the N- and/or C-terminal of the mature protein.

A variant in reference to a peptide may contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also contain nonconservative changes. Variant peptides differ from a native sequence by substitution, deletion or addition of five amino acids or fewer. Variants may also be modified by deletion or addition of amino acids, which have minimal influence on the immunogenicity, secondary structure and hydropathic nature of the polypeptide. A variant may also mean a protein that is substantially identical to a reference protein.

n. Vector

"Vector" as used herein may mean a nucleic acid molecule capable of transporting another nucleic acid to which it has been linked, such as a plasmid. The vector may be capable of extra-chromosomal replication, such as an episome. The vector may be capable of directing expression of the nucleic acid to which it is operatively linked, such as an expression vectors.

2. Butanol Production Cell

Provided herein is a microbial cell suitable for the production of butanol. The cell may be a butanol-producing cell that is recombinant. The butanol-producing cell may be resistant to butanol-associated toxicity. The butanol-producing cell may be a transformed cell comprising a nucleic acid sequence disclosed herein.

a. Butanol Synthesis

The butanol-producing cell may utilize a butanol synthesis system. The butanol synthesis system may comprise a plurality of proteins. The butanol synthesis system may comprise enzymes or variants thereof that catalyze reactions in a butanol synthesis system. The reactions may include the conversion of acetyl-CoA to acetoacetyl-CoA; the coversion of acetoacetyl-CoA to 3-hydroxybutyryl-CoA; the conversion of 3-hydroxybutyryl-CoA to crotonyl-CoA; the conversion of crotonyl-CoA to butyryl-CoA; the conversion of butyryl-CoA to butyraldehyde; and the conversion of butyraldehyde to 1-butanol. The enzymes may include acetyl-CoA acetyl transferase, 3-hydroxybutyryl-CoA dehydrogenase, crotonase, butyryl-CoA dehydrogenase, butyraldehyde dehydrogenase, and butanol dehydrogenase.

(1) Catalysis of Acetyl-CoA to Acetoacetyl-CoA

The butanol synthesis system may comprise an enzymatic reaction that converts acetyl-coA to acetoacetyl-CoA. This reaction may be catalyzed by an acetyl-CoA acetyltransferase. The butanol synthesis system may comprise an acetyl-CoA acetyltransferase or variants thereof. An acetyl-CoA acetyltransferase polypeptide may catalyze the conversion of two molecules of acetyl-CoA to acetoacetyl-CoA and coenzyme A (CoA). The acetyl-CoA acetyltransferase may react with substrates short chain acyl-CoA and acetyl-CoA (classified as E.C. 2.3.1.9 (Enzyme Nomenclature 1992, Academic Press, San Diego). Enzymes with a broader substrate range (E.C. 2.3.1.16) may also be used. Acetyl-CoA acetyltransferases may be available from a number of sources. A source of Acetyl-CoA acetyltransferase may be *E. coli* (GenBank Nos: NP_416728; NC_000913); *C. acetobutylicum* (GenBank Nos: NP_349476.1; NC_003030; NP_149242; NC_001988); *B. subtilis* (GenBank Nos: NP_390297; NC_000964); and *S. cerevisiae* (GenBank Nos: NP_015297; NC_001148).

(2) Catalysis of Acetoacetyl-CoA to 3-Hydroxybutyryl-CoA

The butanol synthesis system may comprise an enzymatic reaction that converts acetoacetyl-CoA to 3-hydroxybutyryl-CoA. The reaction may be catalyzed by a 3-hydroxybutyryl-CoA dehydrogenase polypeptide. The butanol synthesis system may comprise a 3-hydroxybutyryl-CoA dehydrogenase or variants thereof. 3-hydroxybutyryl-CoA dehydrogenase may catalyze the conversion of acetoacetyl-CoA to 3-hydroxybutyryl-CoA. 3-hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA and are classified as E. C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E. C. 1.1.1.157 and E. C. 1.1.1.36, respectively. 3-hydroxybutyryl-CoA dehydrogenases may be available from *C. acetobutylicum* (GenBank NOs: NP_349314), NC_003030), *B. subtilis* (GenBank NOs: AAB09614, U29084), *Ralstonia eutropha* (GenBank NOs: YP_294481, NCJD07347), and *Alcaligenes eutrophus* (GenBank NOs: AAA21973, J04987).

(3) Catalysis of 3-Hydroxybutyryl-CoA to Crotonyl-CoA

The butanol synthesis system may comprise an enzymatic reaction that converts 3-Hydroxybutyryl-CoA to Crotonyl-CoA. This reaction may be catalyzed by a crotonase enzyme. The butanol synthesis system may comprise a crotonase or variants thereof. Crotonase may catalyze the conversion of 3-hydroxybutyryl-CoA to crotonyl-CoA and $H_2O$. Crotonases may have a substrate preference for (S)-3-hydroxybutyryl-CoA or (R)-3-hydroxybutyryl-CoA and are classified as E. C. 4.2.1.17 and E. C. 4.2.1.55, respectively. Crotonases may be available from *E. coli* (GenBank Nos: NP_415911, NC_00913), *C. acetobutylicum* (GenBank NOs: NP_349318, NC_003030), *B. subtilis* (GenBank Nos: CAB13705, Z99113), and *Aeromonas caviae* (GenBank Nos: BAA21816, D88825).

(4) Catalysis of Crotonyl-CoA to Butyryl-CoA

The butanol synthesis system may comprise an enzymatic reaction that converts Crotonyl-CoA to Butyryl-CoA. This reaction may be catalyzed by a butyryl-CoA dehydrogenase enzyme. The butanol synthesis system may comprise a butyryl-CoA dehydrogenase or variants thereof. Butyryl-CoA dehydrogenase may catalyze the conversion of crotonyl-CoA to butyryl-CoA. Butyryl-CoA dehydrogenases may be NADH-dependent or may be NADPH-dependent and may be classified as E.G. 1.3.1.44 and E. C. 1.3.1.38, respectively. Butyryl-CoA dehydrogenases may be available from *C. acetobutylicum* (GenBank NOs: NP_347102, NC_003030), *Euglena gracilis* (GenBank NOs: Q5EU90), AY741582), *Streptomyces collinus* (GenBank NOs: AAA92890, U37135) and *Streptomyces coelicolor* (GenBank Nos: CAA22721, AL939127).

(5) Catalysis of Butyryl-CoA to Butyraldehyde

The butanol synthesis system may comprise an enzymatic reaction that converts Butyryl-CoA to butyraldehyde. This reaction may be catalyzed by a butyraldehyde dehydrogenase enzyme. The butanol synthesis system may comprise a butyraldehyde dehydrogenase or variants thereof. A butyraldehyde dehydrogenase may catalyze the conversion of butyryl-CoA to butyraldehyde, and may use NADH or NADPH as a cofactor. Butyraldehyde dehydrogenases may be available from *Clostridium beijerinckii* (GenBank Nos: AAD31841; AF157306) and *C. acetobutylicum* (GenBank Nos: NP_149325; NC_001988).

(6) Catalysis of Butyraldehyde to 1-Butanol

The butanol synthesis system may comprise an enzymatic reaction that converts Butyraldehyde to 1-Butanol. This reaction may be catalyzed by a butanol dehydrogenase enzyme. The butanol synthesis system may comprise a butanol dehydrogenase or variants thereof. A butanol dehydrogenase polypeptide may catalyze the conversion of butyraldehyde to 1-butanol. A butanol dehydrogenase may use NADH or may use NADPH as a cofactor. Butanol dehydrogenases may be available from *C. acetyobutylicum* (GenBank Nos: NP_149325, NC_001988, this enzyme possesses both aldehyde and alcohol dehydrogenase activity); NP_349892, NC_003030) and *E. coli* (GenBank Nos: NP_417484, NC_000913).

b. Butanol Feedback Inhibition Mutant

The butanol producing cell may be resistant to toxicity associated with increased intracellular and/or extracellular concentrations of butanol. The butanol producing cell may be resistant to inhibitory levels of butanol. The butanol producing cell may have constitutive, unregulated expression of genes or variants thereof involved in butanol production and be resistant to feedback inhibition. The butanol producing cell may have constitutive, unregulated expression of genes involved in butanol production and be resistant to toxic levels of butanol. Examples of a butanol producing strain resistant to feedback inhibition or toxic levels of butanol include the *Clostridium* strain deposited in ATCC (*C. acetobutylicum* BUT R/1; ATCC No. PTA-8515). A butanol producing strain that is resistant to toxic levels of butanol may exhibit increased butanol production above butanol production levels associated with a butanol producing strain that is not resistant to toxic levels of butanol.

A butanol resistant strain may comprise a butanol export protein. The butanol export protein may confer, or correspond to, increased resistance to butanol toxicity.

c. Butanol Export Proteins

The butanol producing cell may utilize butanol export proteins. Specific butanol export proteins may be identified as ideal for the herein described method based upon analyses utilizing an ERGO™ bioinformatics database. The ERGO™ bioinformatics database may be used in in silico analyses of nucleic acids and proteins encoding butanol sythesis enzymes. In silico analyses may determine potential sites of bottlenecks in butanol synthesis that may result from cloning herein described nucleic acids into a host cell.

The export protein may belong to the ATP-binding cassette superfamily of transporters. The export protein may be a multidrug resistance (MDR) protein. The MDR may be ATP-dependent. The MDR protein may be bacterial. The bacterial MDR protein may be ATP-dependent. The butanol export protein may be an OmrA and/or LmrA protein. A bacterial ATP-dependent MDR protein may be OmrA and/or LmrA.

(1) OmrA

The export protein may be an OmrA protein or variant thereof. The OmrA protein or variant thereof may be one selected from Table 1. OmrA may catalyze the transport of butanol via an energy-dependent process, whereby butanol is transported out of a bacterial cell expressing OmrA. OmrA has not previously been known to transport butanol. An OmrA protein may be the *O. oeni* BAA-1163 protein OmrA (GenBank accession: ZP_01543718.1).

(2) LmrA

The butanol export protein may be the transporter, LmrA protein or variant thereof. The LmrA protein or variant thereof may be selected from Table 2. LmrA may catalyze the transport of butanol via an energy-dependent process, whereby butanol is transported out of a bacterial cell expressing LmrA. LmrA has not previously been known to transport butanol. An LmrA protein may be the *Lactococcus lactis* subsp. *cremoris* MG1363 LmrA protein (GenBank Accession No. AAB49750).

TABLE 1

OmrA proteins

| Accession Number | Protein Name/Organism | % Identity to *O. oeni* BAA-1163 OmrA protein (GenBank Accession No. ZP_01543718.1) |
|---|---|---|
| ref\|ZP_01543718.1\| | multidrug resistance ABC transporter ATP binding and permease protein [*Oenococcus oeni* ATCC BAA-1163] | 100 |
| ref\|YP_810879.1\| | ABC-type multidrug transport system, ATPase and permease component [*Oenococcus oeni* PSU-1] | 97 |
| gb\|ABF67604.1 | \| multidrug transporter [*Lactococcus lactis* subsp. *lactis*] | 54 |
| gb\|ABF67599.1\| | multidrug transporter [*Lactococcus lactis* subsp. *lactis*] | 54 |
| gb\|ABF67598.1\| | multidrug transporter [*Lactococcus lactis* subsp. *lactis*] | 54 |
| gb\|ABF67607.1\| | multidrug transporter [*Lactococcus lactis* subsp. *lactis*] | 54 |
| sp\|Q9CHL8\| | LMRA_LACLA Multidrug resistance ABC transporter ATP-binding and permease protein | 54 |
| gb\|ABF67601.1\| multidrug transporter [*Lactococcus lactis* subsp. *lactis*] | multidrug transporter [*Lactococcus lactis* subsp. *lactis*] | 54 |
| ref\|NP_266867.1\| | multidrug resistance ABC transporter ATP binding and permease protein [*Lactococcus lactis* subsp. *lactis* Il1403] | 54 |
| gb\|ABF67605.1\| | multidrug transporter [*Lactococcus lactis* subsp. *lactis*] | 54 |
| ref\|YP_001033128.1\| | multidrug resistance ABC transporter ATP-binding and permease protein [*Lactococcus lactis* subsp. *cremoris* MG1363] | 54 |
| gb\|ABF67597.1\| | multidrug transporter [*Lactococcus lactis* subsp. *cremoris*] | 54 |
| gb\|ABF67600.1\| | multidrug transporter [*Lactococcus lactis* subsp. *lactis*] | 54 |
| ref\|YP_796084.1\| | ABC-type multidrug transport system, ATPase and permease component [*Lactobacillus brevis* ATCC 367] | 52 |
| ref\|ZP_01274735.1\| | ABC transporter, transmembrane region:ABC transporter related [*Lactobacillus reuteri* 100-23] | 53 |
| ref\|YP_394844.1\| | Multidrug ABC exporter, ATP-binding and membrane-spanning/permease subunits [*Lactobacillus sakei* subsp. *sakei* 23K] | 54 |
| ref\|YP_001270631.1\| | ABC transporter related [*Lactobacillus reuteri* F275] | 53 |
| ref\|NP_786297.1\| | multidrug ABC transporter, ATP-binding and permease protein [*Lactobacillus plantarum* WCFS1] | 53 |

TABLE 1-continued

OmrA proteins

| Accession Number | Protein Name/Organism | % Identity to O. oeni BAA-1163 OmrA protein (GenBank Accession No. ZP_01543718.1) |
|---|---|---|
| ref\|ZP_01695678.1\| | ABC transporter related [*Bacillus coagulans* 36D1] | 54 |

TABLE 2

LmrA proteins

| Accession No. | Protein Name/Organism | % Identity to *Lactococcus lactis* subsp. *cremoris* MG1363 LmrA (GenBank Accession No. AAB49750) |
|---|---|---|
| ref\|YP_001033128.1\| | multidrug resistance ABC transporter ATP-binding and permease protein [*Lactococcus lactis* subsp. *cremoris* MG1363] | 100 |
| gb\|ABF67597.1\| | multidrug transporter [*Lactococcus lactis* subsp. *cremoris*] | 99 |
| sp\|Q9CHL8\| | LMRA_LACLA Multidrug resistance ABC transporter ATP-binding and permease protein | 96 |
| gb\|ABF67598.1\| | multidrug transporter [*Lactococcus lactis* subsp. *lactis*] | 96 |
| gb\|ABF67599.1\| | multidrug transporter [*Lactococcus lactis* subsp. *lactis*] | 96 |
| gb\|ABF67601.1\| | multidrug transporter [*Lactococcus lactis* subsp. *lactis*] | 96 |
| gb\|ABF67604.1\| | multidrug transporter [*Lactococcus lactis* subsp. *lactis*] | 96 |
| gb\|ABF67607.1\| | multidrug transporter [*Lactococcus lactis* subsp. *lactis*] | 96 |
| gb\|ABF67605.1\| | multidrug transporter [*Lactococcus lactis* subsp. *lactis*] | 96 |
| gb\|ABF67600.1\| | multidrug transporter [*Lactococcus lactis* subsp. *lactis*] | 96 |
| ref\|NP_266867.1\| | multidrug resistance ABC transporter ATP binding and permease protein [*Lactococcus lactis* subsp. *lactis* I11403] | 96 |
| ref\|ZP_01695678.1\| | ABC transporter related [*Bacillus coagulans* 36D1] | 62 |
| ref\|YP_805121.1\| | ABC-type multidrug transport system, ATPase and permease component [*Pediococcus pentosaceus* ATCC 25745] | 61 |
| ref\|NP_786297.1\| | multidrug ABC transporter, ATP-binding and permease protein [*Lactobacillus plantarum* WCFS1] | 59 |

The butanol-producing cell may be able to tolerate various toxic levels of butanol. The toxic levels of butanol may be greater than 10 g/L, 11 g/L, 12 g/L, 13 g/L, 14 g/L, 15 g/L, 16 g/L, 17 g/L, 18 g/L, 19 g/L, 20 g/L, 21 g/L, 22 g/L, 23 g/L, 24 g/L, 25 g/L, 26 g/L, 27 g/L, 28 g/L, 29 g/L, 30-40 g/L, 40-60 g/L, and between 60-100 g/L.

d. Host Cells

The butanol-producing cell may be derived from any microbial host cell familiar to those skilled in the art. The host cell may be any member of the genera *Clostridium, Lactococcus, Lactobacillus, Zymomonas, Escherichia, Salmonella, Rhodococcus, Pseudomonas, Bacillus, Lactobacillus, Oenococcus, Enterococcus, Alcaligenes, Klebsiella, Paenibacillus, Arthrobacter, Corynebacterium, Brevibacterium, Pichia, Candida, Hansenula* and *Saccharomyces*. The host cell may be *Escherichia coli, Lactococcus lactis, Clostridium acetobutylicum, Clostridium beijerinckii, Bacillus licheniformis, Alcaligenes eutrophus, Oenococcus oeni, Paenibacillus macerans, Rhodococcus erythropolis, Pseudomonas putida, Lactobacillus plantarum, Enterococcus faecium, Enterococcus gallinarium, Enterococcus facecalis, Baceillus subtilis*, and *Saccharomyces cerevisiae*. A host cell that can endogenously synthesize butanol may be *Clostridium beijerinckii* or *Clostridium acetobutylicum*. A host cell that can endogenously export butanol may be *Oenococcus oeni* or *Lactococcus lactis*. A host cell may be resistant to butanol. The host cell may be ATCC No. PTA-8515.

e. Nucleic Acid

Also provided herein is a nucleic acid. The nucleic acid may encode a butanol export protein or a variant thereof. The nucleic acid may encode a protein resistant to feedback inhibition of butanol or a variant thereof. The nucleic acid may encode a protein resistant to toxic levels of butanol or a variant thereof. A nucleic acid may also encode a component of the butanol synthesis system or variants thereof. The nucleic acid may encode a butanol resistant gene or variant thereof. The nucleic acid may be derived from a cell deposited in ATCC (*C. acetobutylicum* BUT R/1; ATCC No. PTA-8515). The nucleic acid may comprise native sequences such as an endogenous sequence.

The nucleic acid may be combined with other DNA sequences, such as promoters, polyadenylation signals, polyhistidine signals additional restriction enzyme sites, multiple cloning sites, other coding segments, and the like. Nucleic acids may also be capable of hybridizing under moderately stringent conditions and specifically binding to a nucleic of an agent.

(1) Vector

A vector may comprise the nucleic acid. The vector may be an expression vector. The vector may comprise a nucleic acid sequence or plurality thereof encoding the amino acid sequences. The vector may express the nucleic acid in a heterologous expression alone or in combination with a cell's endogenous expression of omrA, lmrA, and/or genes encoding proteins of a butanol synthesis system.

The expression vector may include one or more control sequences capable of effecting and/or enhancing the expression of the agent. Control sequences that are suitable for expression in prokaryotes, for example, include a promoter sequence, an operator sequence, and a ribosome-binding site. Control sequences for expression in eukaryotic cells may include a promoter, an enhancer, and a transcription termination sequence (i.e. a polyadenylation signal).

A vector may also include other sequences, such as, for example, nucleic acid sequences encoding a signal sequence or an amplifiable gene. A signal sequence may direct the secretion of a polypeptide fused thereto from a cell expressing the protein. In the expression vector, nucleic acid encoding a signal sequence may be linked to a polypeptide coding sequence so as to preserve the reading frame of the polypeptide coding sequence.

3. Butanol Production Methods

Provided herein is a method of bioproducing butanol from carbon sources. The method may use a butanol-producing cell comprising a butanol synthesis pathway and/or a protein that exports butanol. The butanol producing cell may be resistant to inhibitory or toxic levels of butanol. The butanol producing cell may be resistant to inhibitory or toxic levels of butanol and may comprise a butanol synthesis pathway and a protein that exports butanol. The butanol-producing cell may be contacted with a fermentable carbon substrate under conditions whereby butanol is produced.

Host cell culture conditions may allow transcription, translation, and protein transport between cellular compartments. Factors that affect these processes are well-known and include, for example, DNA/RNA copy number; factors that stabilize DNA; nutrients, supplements, and transcriptional inducers or repressors present in the culture medium; temperature, pH and osmolarity of the culture; and cell density. The adjustment of these factors to promote expression in a particular vector-host cell system is within the level of skill in the art. Principles and practical techniques for maximizing the productivity of in vitro mammalian cell cultures, for example, may be found in Mammalian Cell Biotechnology: a Practical Approach (Butler ed., IRL Press (1991).

Any of a number of well-known techniques for large- or small-scale production of proteins may be employed in expressing a nucleic acid and production of a target compound. These may include the use of a shaken flask, a fluidized bed bioreactor, a roller bottle culture system, and a stirred tank bioreactor system. Cell culture may be carried out in a batch, fed-batch, or continuous mode.

(1) Carbon Substrate

The butanol-producing cell may be contacted with a carbon substrate. The carbon substrate may be one or more of hydrolyzed or unhydrolyzed potatoes or potato waste, sulfite waste liquor, sugar beet, wheat, rye, oats, $CO_2$, distillers dry grain solids (DDGS), corn, soy molasses, whey permeate, Jerusalem artichokes, corn fiber, and/or molasses. The DDGS may be a by-product of the corn dry milling ethanol industry. The sulfite waste liquor may be a by-product of the paper industry and may contain glucose, xylose, and/or arabinose.

Upstream processing may be required for the production of butanol from a substrate. Upstream processing may include dilution, concentration, removal of insoluble solids, milling, sieving, centrifugation, saccharification, and/or reverse osmosis. Cellulosic biomass may require hydrolysis. The hydrolysis may require acid and/or enzymatic treatment of the biomass. DDGS may be used as a substrate for butanol fermentation following hydrolysis of the cellulosics. Sugar degradation products, which may inhibit fermentation, may be removed. Inulinase may be used for treating a carbon source.

Increasing or decreasing temperature of a carbon substrate during fermentation may be useful during the butanol production method. An increase or decrease in temperature may result in enhanced tolerance of the production host to the butanol product.

(2) Isolating Butanol Product

The produced butanol may be isolated from the fermentation medium using methods known in the art. Solids may be removed from the fermentation medium by centrifugation, filtration, decantation, or the like. The butanol may be isolated from the fermentation medium using methods such as distillation, liquid-liquid extraction, or membrane-based separation. Because butanol forms a low boiling point, azeotropic mixture with water, distillation may be used to separate the mixture up to its azeotropic composition. Distillation may be used in combination with another separation method to obtain separation around the azeotrope. Methods that may be used in combination with distillation to isolate and purify butanol may include decantation, liquid-liquid extraction, adsorption, and membrane-based techniques. Additionally, butanol may be isolated using azeotropic distillation using an entrainer.

Butanol-water mixtures may form a heterogeneous azeotrope so that distillation may be used in combination with decantation to isolate and purify the butanol. The butanol containing fermentation broth may be distilled to near the azeotropic composition. The azeotropic mixture may be condensed, and the butanol separated from the fermentation medium by decantation. The decanted aqueous phase may be returned to the first distillation column as reflux. The butanol decanted organic phase may be further purified by distillation in a second distillation column.

The butanol may also be isolated from the fermentation medium using liquid-liquid extraction in combination with distillation. The butanol may be extracted from the fermentation broth using liquid-liquid extraction with a suitable solvent. The butanol-containing organic phase may then be distilled to separate the butanol from the solvent.

Distillation in combination with adsorption may also be used to isolate butanol form the fermentation medium. The medium containing the butanol may be distilled to near the azeotropic composition and then the remaining water may be removed by use of an adsorbent, such as molecular sieves.

Distillation in combination with pervaporation may be used to isolate and purify the butanol from the fermentation medium. The fermentation broth containing the butanol may be distilled to near azeotropic composition, and the remaining water may be removed by pervaporation through a hydrophilic membrane.

EXAMPLE 1

Cloning omrA Nucleic Acid

The following primers were used for PCR, cloning and sequencing of the nucleic acid fragment comprising omrA gene from *Oenococcus oeni*. The nucleic acid also comprised the omrA native promoter.

TABLE 3

| Primers for PCR, Cloning and Sequencing of omrA Gene | |
|---|---|
| 5'-TAA ACA AAT GCG GCA GCA TCA AC-3' | (SEQ ID NO:1) |
| 5'-TAA ATT ATT TGG TAA CAA ATT GTT CAG-3' | (SEQ ID NO:2) |
| 5'-CAA AAG CAA AGA TTT CGG GC-3' | (SEQ ID NO:3) |
| 5'-TGT TCA CAA CTG ATT GGC AC-3' | (SEQ ID NO:4) |
| 5'-GAC AAT GGT AAT GAT GGG C-3' | (SEQ ID NO:5) |
| 5'-ATT GCT CGT GCT TTC TTG CGG G-3' | (SEQ ID NO:6) |
| 5'-GTC TTT GTT GTT GAT GCT GC-3' | (SEQ ID NO:7) |
| 5'-TGG TCG TGC TAT CAA GAT G-3' | (SEQ ID NO:8) |

TABLE 3-continued

Primers for PCR, Cloning and Sequencing of omrA Gene

5'-AAA GCG AAC AAG CCC ATC-3'        (SEQ ID NO:9)

5'-TCC TGT GAT ACA AAG CCG-3'        (SEQ ID NO:10)

The primers used for cloning the omrA ORF nucleic acid without its endogenous promoter were:

(1)
5'-TGA CAT ATG TCA GAA AGA ACG CT-3' (SEQ ID NO:11)

(2)
5'-TCA GCT CAG CTT ATT TGG TAA CA-3' (SEQ ID NO:12)

The omrA gene of *O. oeni* was isolated from the bacterium by a whole-cell PCR procedure using Easy-A high fidelity PCR cloning enzyme and primers corresponding to the beginning and to the end of the gene DNA sequence. The products of PCR reaction were loaded on 0.7% agarose gel. DNA fragments were cut out from the gel and purified using QIAquick gel extraction kit. Fragments corresponding to omrA (1800 bp) gene and pET9a vector were digested with BlpI and NdeI at 37° C. for 2 hours and products of reaction were loaded on 0.7% agarose gel. Fragments were cut out from the gel and purified by QIAquick Gel Extraction Kit.

The DNA ligation reaction of the omrA fragment into the plasmid vector, pET9a, was performed by mixing 2 µl of pET9a DNA with 15 µl of omrA (1800) DNA, 2 µl of ligase buffer and 1 µl of T4 DNA ligase. The mixture was incubated at 16° C. overnight. The plasmid transformation was performed using 1 µl of the ligation mixture was added to 20 µl of TUNER (DE3) competent *E. coli* cells, incubated on ice for 5 min, then heated at 42° C. for 30 sec and placed on ice for 2 min. 80 µl of SOC medium was added to the mixture and incubated at 37° C. for 1 hour with shaking. 5 µl of the transformation mixture were plated out on LB agar plates with 30 µl/ml kanamycin. Plates were incubated at 37° C. overnight. Kanamycin-resistant transformants were tested for the presence of the omrA gene insert using whole cell PCR technique. 10 clones were tested and none was found to contain 1800 bp insertion corresponding to omrA fragment. The result was confirmed by restriction analysis (BlpI and NdeI) of plasmid DNA isolated by "Wizard Plus Miniprep" kit (Promega).

The omrA gene of *O. oeni* containing its native promoter was isolated from the bacterium by whole cells PCR procedure using Easy-A high fidelity PCR cloning enzyme and primers corresponding to DNA sequence located approximately 400 bp prior to the beginning of omrA gene and corresponding to the end of the gene sequence. The products of PCR reaction were loaded on 7% agarose gel. DNA fragments were cut out from the gel and purified using QIAquick gel extraction kit.

Cloning was performed by mixing 2 µl omrA (2200 bp) DNA with 1 µl of pCR-II TOPO DNA, 1 µl of standard salt solution and 2 µl of water. Incubation continued for 17 min at room temperature. 2 µl of cloning mixture were mixed with "One Shot Chemical competent *E. coli*" and placed on ice for 17 min. After that cells were heat-shocked at 42° C. for 30 sec and returned to ice for 2 min. 250 µl of SOC medium were added to the reaction mixture and incubated at 37° C. for 1 hour with shaking. The transformation mixture was plated out on LB agar containing 50 µg/ml of kanamycin and 40 µg/ml of X-gal. Plates were incubated at 37° C. overnight.

Kanamycin-resistant transformants were analyzed by whole cell PCR. The 2200 bp fragment of DNA was found in the recombinant plasmid. The presence of the insertion was verified by restriction analysis (EcoRI) of plasmid DNA isolated and purified by Wizard Plus Miniprep kit (Promega). The recombinant plasmid omrA2200/pCR-II TOPO was sequenced using ABI 3700 Sequencing Analyzer.

EXAMPLE 2

*C. acetobutylicum* and *O. oeni* Tolerance to Butanol

Cell growth was determined by the optical density at 600 nm[1] (Spectrophotometer Beckman DU640). The ability of the strains to tolerate and grow at 37° C. (*Clostridium acetobutylicum*) or 30° C. (*Oenococcus oeni*) in presence of various levels of butanol was examined in 5 ml plastic test tubes under batch conditions. See FIG. 1. *Clostridium acetobutylicum* was incubated in an anaerobic chamber under a hydrogen atmosphere (90%) and carbon dioxide (10%). Various levels of butanol were added to the medium in the tube before inoculation and the tubes were incubated at 37° C. *Escherichia coli* cells were grown in Luria-Bertani (LB) medium, while *Oenococcus oeni* and *Lactococcus lactis* strains were propogated in *Lactobacilli* MRS broth (Criterion, Hardy Diagnostics) and *Clostridium acetobutylicum* was cultured in Reinforced Clostridial Medium (Difco, Detroit, Mich.). According to FIG. 1, the level of butanol at which growth was reduced to 50% in *C. acetobutylicum* and *O. oeni* is 0.8% and 1.4%, respectively. This effect may be due to the presence in the *O. oeni* genome of the endogenous gene, omrA.

EXAMPLE 3 omrA+ *E. coli* Tolerance to Butanol

The omrA gene was isolated from the *O. oeni* chromosome and cloned into the pCR-II TOPO vector. omrA/pCR-II TOPO/TOP10 *E. coli* cells were slightly more resistant to butanol than the *E. coli* TOPO10 host cells. See FIG. 2.

Figure 2:
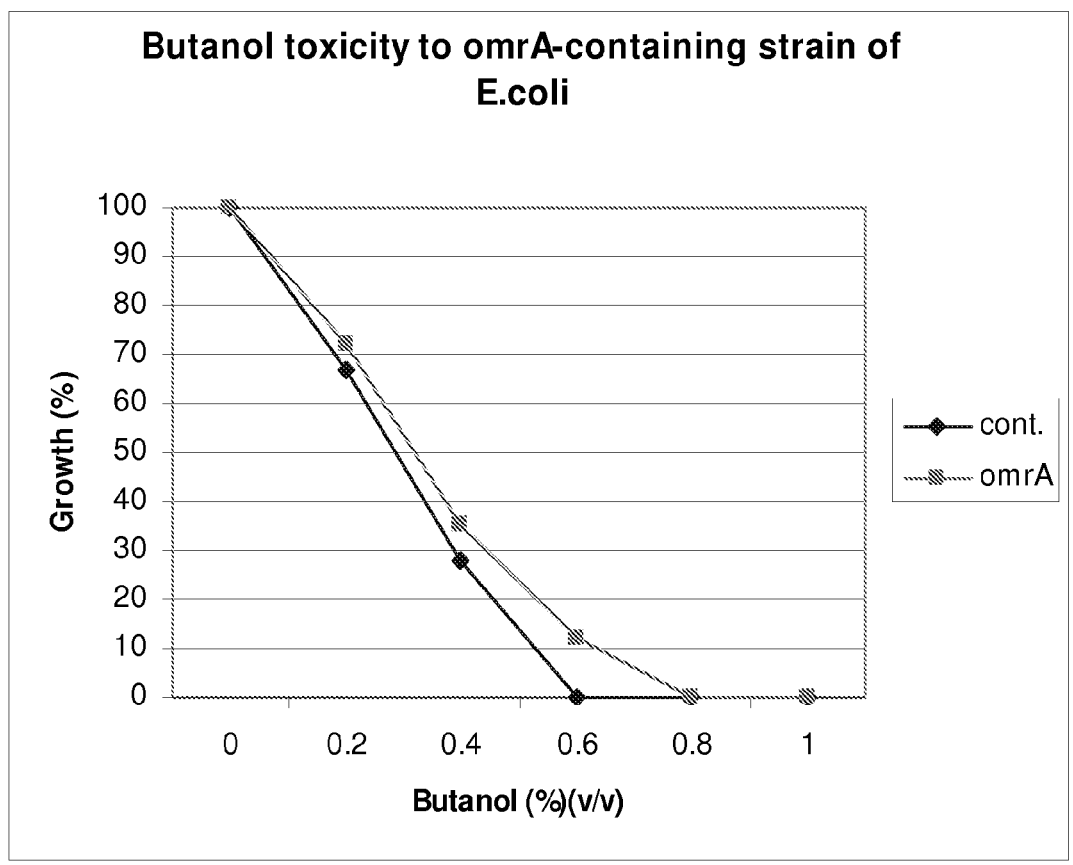
FIG. 2 shows that omrA/pCR-II TOPO/TOP10 *E. coli* cells (omrA—square) are slightly more resistant to butanol than the *E. coli* TOPO10 host cells (cont.-diamond).
Figure 3:
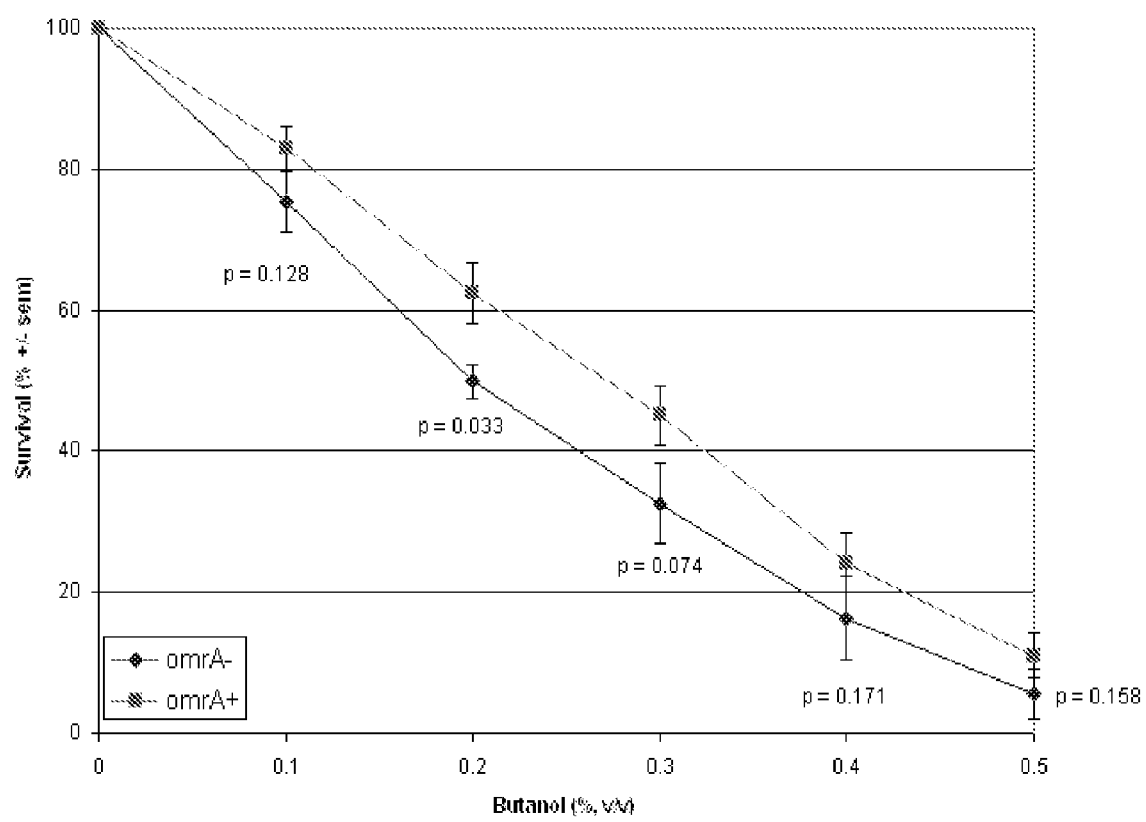
FIG. 3 shows survival rates of *E. coli* strains with and without an omrA-plasmid in the presence of varying levels of butanol.

A second experiment confirmed the results shown in FIG. 2. Survival rates of *E. coli* strains with and without the omrA-plasmid were determined. The *E. coli* strain containing the heterologous omrA gene increased bacterial survival significantly compared with the host strain with no omrA gene. See FIG. 3. For this experiment, the omrA gene was inserted into the expression plasmid pCR-Blunt II-TOPO (invitrogen, Carlsbad, Calif.) hosted by the TOP10 *E. coli* strain [F-mcrA Δ (mcr-hsdRMS-mcrBC) Φ)80lacZ ΔM15 ΔlacX74 recA1 deoR araD139 Δ (ara-leu)7697 galU galK rpsL (Str$^R$) endA1 nupG]. The plasmid with no insertion was used as a control. Flasks (50 ml) containing 10 ml of LB broth with 50 µg/ml kanamycin were inoculated with 100 µl of bacterial cells grown overnight at 37° C. in the same medium and incubated at 37° C. with aeration (200 rpm) for 4 hours. Bacterial growth was stopped by adding chloramphenicol (100 µg/ml) and optical density of cell cultures measured spectrophotometrically at 600 nm.

EXAMPLE 4

Effect of Butanol on *C. acetobutylicum* 824 and But-R/1 (Mutant) Growth

But-R/1 mutant (ATCC No. PTA-8515), a derivative of *C. acetobutylicum* ATCC 824, was produced via long-term incubation of wild-type *C. acetobutylicum* 824 in reinforced *Clostridium* medium ("RCM") with glucose (0.5%) and butanol (2.5% v/v) under anaerobic conditions at 37° C. When turbidity developed, the bacterial suspension was spread onto RCM agar with 2.5% butanol. Single colonies of butanol-resistant mutants appeared after 5 days of incubation at 37° C. Mutants were purified twice using RCM agar containing 2.5% of butanol. The But-R/1 mutant that produced the largest colonies was subsequently tested in liquid medium. Cells were grown for 3 days in RCM medium in an anaerobic jar at 37° C. Optical density of cell suspensions was measured at 600 nm spectrophotometrically. See Table 4.

TABLE 4

Growth inhibition of *Clostridium acetobutylicum* ATCC 824 (wild type) and BUT-R/1 mutant by butanol

| Butanol (%)(v/v) | WT | Mutant |
| --- | --- | --- |
| 0.3 | 8.4 | 0 |
| 0.6 | 40.4 | 0 |
| 0.9 | 56.1 | 0 |
| 1.2 | 89.7 | 23.2 |
| 1.5 | 94.2 | 73.8 |
| 1.8 | 99.5 | 84.2 |

EXAMPLE 5

Butanol Production in Butanol-Resistant Strains

To determine the relative production levels of butanol in the wild-type and butanol-resistant mutant (ButR/1; ATCC No. PTA-8515) *C. acetobutylicum* cells, an enzymatic, colorimetric butanol detection assay was developed. This assayed was used to determine butanol production levels in wild-type and ButR/1 mutant cells (under several separate fermentation experiments). The results from these experiments are shown in Table 5, wherein each butanol production value is the average of two separate fermentation experiments.

TABLE 5

| Experiment | Butanol Production (mg/ml) | | Stimulation in butanol production (%) |
| --- | --- | --- | --- |
| | Wild-type | Mutant | |
| 1 | 7.013 | 8.561 | 22 |
| 2 | 4.870 | 6.359 | 31 |
| 3 | 4.019 | 10.685 | 165 |

The results demonstrate that butanol production is increased in the *C. acetobutylicum* ButR/1 mutant as compared to wild type *C. acetobutylicum*. The average percent increase in butanol production is approximately 39%.

With respect to the fermentation conditions, bacterial cells were incubated in capped tubes (7 ml capacity) containing 5 ml of RCM medium for 24 hours at 37° C. under $N_2$ atmosphere.

A colorimetric of butanol concentration assay was devised using a yeast alcohol dehydrogenase (*S. cerevisiae*; Sigma). The enzymatic butanol oxidation was measured as a phenazine methosulfate mediated 2-(p-iodophenyl)-3-(p-nitrophenyl)-5-phenyl tetrazolium chloride reduction reaction. The incubation medium (total volume, 1 ml) contained (a final concentration): alcohol dehydrogenase, 1.5 unit/ml; Tris-HCl (pH 7.4), 0.1M; βNAD, 1 mM; phenazine methosulfate, 0.12 mM; 2-(p-iodophenyl)-3-(p-nitrophenyl)-5-phenyl tetrazolium chloride, 0.67 mM; SDS, 1%; EDTA, 0.1 mM. The reaction was initiated by adding alcohol dehydrogenase to the mixture containing cell-free sample of fermentation broth. After 15 minutes of incubation at room temperature, the reaction was terminated by adding HCl (0.36N final concentration). The absorbance was measured spectrophotometrically at 570 nm (against a blank that contained all of the reagents except butanol). A calibration curve was generated using butanol (Sigma). A linearity in the butanol assay standard curve was observed in the range of 10 to 110 μmoles per sample.

We claim:

1. An isolated butanol-producing microbial cell comprising a heterologous nucleic acid encoding a multi-drug resistance protein selected from the group consisting of OmrA and LmrA.

2. The microbial cell of claim 1, wherein the cell is resistant to butanol-associated toxicity.

3. The microbial cell of claim 1, wherein the cell further comprises a nucleic acid encoding a polypeptide that catalyzes a substrate to product conversion selected from the group consisting of:
   (a) acetyl-CoA to acetoacetyl-CoA;
   (b) acetoacetyl-CoA to 3-hydroxybutyryl-CoA;
   (c) 3-hydroxybutyryl-CoA to crotonyl-CoA;
   (d) crotonyl-CoA to butyryl-CoA;
   (e) butyryl-CoA to butyraldehyde; and
   (f) butyraldehyde to 1-butanol.

4. The microbial cell of claim 3, wherein the nucleic acid encoding a polypeptide that catalyzes a substrate to product conversion is heterologous to the microbial host cell.

5. The microbial cell of claim 1, wherein the cell is selected from the group consisting of *Clostridium beijerinckii* and *Clostridium acetobutylicum*.

6. An isolated butanol-producing microbial cell comprising a heterologous nucleic acid encoding a polypeptide that catalyzes a substrate to product conversion selected from the group consisting of:
   (a) acetyl-CoA to acetoacetyl-CoA;
   (b) acetoacetyl-CoA to 3-hydroxybutyryl-CoA;
   (c) 3-hydroxybutyryl-CoA to crotonyl-CoA;
   (d) crotonyl-CoA to butyryl-CoA;
   (e) butyryl-CoA to butyraldehyde; and
   (f) butyraldehyde to 1-butanol, wherein the microbial cell is selected from the group consisting of Qenococcus Qeni and Lactococcus lactis.

7. The microbial cell of claim 6, wherein the cell is resistant to butanol-associated toxicity.

8. An isolated butanol-resistant microbial cell, wherein the cell is ATCC No. PTA 8515.

9. The isolated butanol-resistant microbial cell of claim 7, wherein the cell comprises a heterologous nucleic acid encoding a polypeptide that exports butanol.

10. A method for increasing butanol production in a microbial cell comprising:
   (a) providing a microbial cell selected from any one of claims 1, 2, 3, 4, 5, 6, 7, 8 or 9; and
   (b) contacting the microbial host cell with a carbon substrate.

11. The method of claim 10, wherein the microbial cell is characterized by increased resistance to butanol.

12. The method of claim 10, wherein the carbon substrate is a fermentable carbon substrate.

13. The method of claim 12, wherein the fermentable carbon substrate is selected from the group consisting of potato, potato waste, sulfite waste liquor, sugar beet, wheat, rye, oats, $CO_2$, distillers dry grain solids (DDGS), corn, soy molasses, whey permeate, Jerusalem artichokes, corn fiber, and molasses.

* * * * *

SEQUENCE LISTING

<160> NUMBER OF SEQ ID NOS: 12

<210> SEQ ID NO 1
<211> LENGTH: 23
<212> TYPE: DNA
<213> ORGANISM: Artificial
<220> FEATURE:
<223> OTHER INFORMATION: Primer for PCR, cloning and sequencing of omrA
      gene.

<400> SEQUENCE: 1
taaacaaatg cggcagcatc aac                                            23

<210> SEQ ID NO 2
<211> LENGTH: 27
<212> TYPE: DNA
<213> ORGANISM: Artificial
<220> FEATURE:
<223> OTHER INFORMATION: Primer for PCR, cloning and sequencing of omrA
      gene.

<400> SEQUENCE: 2
taaattattt ggtaacaaat tgttcag                                        27

```
<210> SEQ ID NO 3
<211> LENGTH: 20
<212> TYPE: DNA
<213> ORGANISM: Artificial
<220> FEATURE:
<223> OTHER INFORMATION: Primer for PCR, cloning and sequencing of omrA
      gene.

<400> SEQUENCE: 3
caaaagcaaa gatttcgggc                                                  20

<210> SEQ ID NO 4
<211> LENGTH: 19
<212> TYPE: DNA
<213> ORGANISM: Artificial
<220> FEATURE:
<223> OTHER INFORMATION: Primer for PCR, cloning and sequencing of omrA
      gene.

<400> SEQUENCE: 4
tgtcacaact gattggcac                                                   19

<210> SEQ ID NO 5
<211> LENGTH: 19
<212> TYPE: DNA
<213> ORGANISM: Artificial
<220> FEATURE:
<223> OTHER INFORMATION: Primer for PCR, cloning and sequencing of omrA
      gene.

<400> SEQUENCE: 5
gacaatggta atgatgggc                                                   19

<210> SEQ ID NO 6
<211> LENGTH: 22
<212> TYPE: DNA
<213> ORGANISM: Artificial
<220> FEATURE:
<223> OTHER INFORMATION: Primer for PCR, cloning and sequencing of omrA
      gene.

<400> SEQUENCE: 6
attgctcgtg ctttcttgcg gg                                               22

<210> SEQ ID NO 7
<211> LENGTH: 20
<212> TYPE: DNA
<213> ORGANISM: Artificial
<220> FEATURE:
<223> OTHER INFORMATION: Primer for PCR, cloning and sequencing of omrA
      gene.

<400> SEQUENCE: 7
gtctttgttg ttgatgctgc                                                  20

<210> SEQ ID NO 8
<211> LENGTH: 19
<212> TYPE: DNA
<213> ORGANISM: Artificial
<220> FEATURE:
<223> OTHER INFORMATION: Primer for PCR, cloning and sequencing of omrA
      gene.

<400> SEQUENCE: 8
tggtcgtgct atcaagatg                                                   19
```

-continued

```
<210> SEQ ID NO 9
<211> LENGTH: 18
<212> TYPE: DNA
<213> ORGANISM: Artificial
<220> FEATURE:
<223> OTHER INFORMATION: Primer for PCR, cloning and sequencing of omrA
      gene.

<400> SEQUENCE: 9
aaagcgaaca agcccatc                                                   18

<210> SEQ ID NO 10
<211> LENGTH: 18
<212> TYPE: DNA
<213> ORGANISM: Artificial
<220> FEATURE:
<223> OTHER INFORMATION: Primer for PCR, cloning and sequencing of omrA
      gene.

<400> SEQUENCE: 10
tcctgtgata caaagccg                                                   18

<210> SEQ ID NO 11
<211> LENGTH: 23
<212> TYPE: DNA
<213> ORGANISM: Artificial
<220> FEATURE:
<223> OTHER INFORMATION: Primer for PCR, cloning and sequencing of omrA
      gene.

<400> SEQUENCE: 11
tgacatatgt cagaaagaac gct                                             23

<210> SEQ ID NO 12
<211> LENGTH: 23
<212> TYPE: DNA
<213> ORGANISM: Artificial
<220> FEATURE:
<223> OTHER INFORMATION: Primer for PCR, cloning and sequencing of omrA
      gene.

<400> SEQUENCE: 12
tcagctcagc ttatttggta aca                                             23
```